United States Patent
He et al.

(10) Patent No.: US 10,619,100 B2
(45) Date of Patent: Apr. 14, 2020

(54) CHIRAL COMPOUND, LIQUID CRYSTAL MATERIAL, PREPARATION METHOD THEREOF, AND DISPLAY DEVICE

(71) Applicants: BOE Technology Group Co., Ltd., Beijing (CN); Hefei Xinsheng Optoelectronics Technology Co., Ltd., Hefei (CN)

(72) Inventors: Xiaoyue He, Beijing (CN); Lei Zhang, Beijing (CN); Tsung Chieh Kuo, Beijing (CN); Ming Hu, Beijing (CN)

(73) Assignees: BOE TECHNOLOGY GROUP CO., LTD., Beijing (CN); HEFEI XINSHENG OPTOELECTRONICS TECHNOLOGY CO., LTD, Anhui (CN)

( * ) Notice: Subject to any disclaimer, the term of this patent is extended or adjusted under 35 U.S.C. 154(b) by 164 days.

(21) Appl. No.: 15/735,381

(22) PCT Filed: Jun. 27, 2017

(86) PCT No.: PCT/CN2017/090318
§ 371 (c)(1),
(2) Date: Dec. 11, 2017

(87) PCT Pub. No.: WO2018/010540
PCT Pub. Date: Jan. 18, 2018

(65) Prior Publication Data
US 2019/0241810 A1    Aug. 8, 2019

(30) Foreign Application Priority Data

Jul. 14, 2016 (CN) .......................... 2016 1 0554675

(51) Int. Cl.
| | | |
|---|---|---|
| G02F 1/1333 | (2006.01) | |
| C09K 19/58 | (2006.01) | |
| C07C 245/08 | (2006.01) | |
| C09K 19/56 | (2006.01) | |
| C09K 19/60 | (2006.01) | |

(52) U.S. Cl.
CPC .......... C09K 19/586 (2013.01); C07C 245/08 (2013.01); C09K 19/56 (2013.01); C09K 19/601 (2013.01); G02F 1/1333 (2013.01)

(58) Field of Classification Search
CPC ... C09K 19/586; C09K 19/601; G02F 1/1333; C07C 245/08
USPC ...................................................... 252/299.01
See application file for complete search history.

(56) References Cited

U.S. PATENT DOCUMENTS

| 5,393,644 A | 2/1995 | Etzbach et al. |
|---|---|---|
| 2002/0114902 A1 | 8/2002 | Chuard et al. |

FOREIGN PATENT DOCUMENTS

| CN | 102093377 A | 6/2011 |
|---|---|---|
| CN | 104496933 A | 4/2015 |
| WO | 9811077 A1 | 3/1998 |

OTHER PUBLICATIONS

First Office Action, including Search Report, for Chinese Patent Application No. 201610554675.X, dated Feb. 19, 2019, 12 pages.
Mandal Braja K. et al., "Novel photo-crosslinked nonlinear optical polymers," Departments of Chemistry, Physics, and Plastics, University of Lowell, Massachusetts, article PF 160273CNI, Dec. 31, 1991, 6 pages.
International Search Report and English translation of International Search Report for International Application No. PCT/CN2017/090318, dated Sep. 28, 2017, 6 pages.
Written Opinion and English translation of Box No. 5 of Written Opinion for International Application No. PCT/CN2017/090318, dated Sep. 28, 2017, 6 pages.

*Primary Examiner* — Geraldina Visconti
(74) *Attorney, Agent, or Firm* — Westman, Champlin & Koehler, P.A.

(57) ABSTRACT

The present disclosure relates to a chiral compound of formula (I), wherein $R^1$, $R^{1'}$, $R^2$, $R^{2'}$, n, n', m and m' are as defined in the specification. The present disclosure also relates to the preparation of the chiral compound. A cholesteric liquid crystal can be obtained by adding the compound to a nematic liquid crystal material, and the helical twisting power constant of the chiral additive can be changed by irradiating, so as to expand the reflection band width. As such, the present disclosure further relates to the use of the chiral compound in preparing a cholesteric liquid crystal material, a cholesteric liquid crystal material comprising the chiral compound of the present disclosure, and a display device comprising the cholesteric liquid crystal material.

20 Claims, 3 Drawing Sheets

CHIRAL COMPOUND, LIQUID CRYSTAL MATERIAL, PREPARATION METHOD THEREOF, AND DISPLAY DEVICE

The present is a Section 371 National Stage Application of International Application No. PCT/CN2017/090318, filed Jun. 27, 2017 which is not yet published, and application claims a priority of Chinese Patent Application No. 201610554675.X, filed on Jul. 14, 2016, and the entire contents thereof are incorporated herein as a part of the present application by reference.

TECHNICAL FIELD

The present disclosure relates to the technical field of display. Particularly, the present disclosure relates to a chiral compound, a cholesteric liquid crystal material comprising the chiral compound, preparation methods for the chiral compound and the cholesteric liquid crystal material, and a display device comprising the cholesteric liquid crystal material.

BACKGROUND

Recently, with the development of electronic and microelectronic technologies, colors play a more and more important role in data storage and display, and the adjustment and control of colors are one of the major features of modern display technology. Colors of many living beings in nature, such as colors of beetles' elytra and butterflies' wings, are derived from their microstructures. Research suggests that the microstructure of beetles' elytra is similar to that of cholesteric liquid crystal. The unique helical structure of cholesteric liquid crystal determines its special optical properties, such as selective reflection, circular dichroism and the like. When the wavelength ($\lambda$o) of an incident light is matched with the pitch (p) of a cholesteric liquid crystal, that is, $\lambda o = n \times p$, (n is the average reflectivity of the cholesteric liquid crystal), the light is reflected and the reflected light is a circularly polarized light, the rotation direction of which is in conformity with the helical structure of the cholesteric liquid crystal. Therefore, the wavelength of the reflected light can be adjusted by changing the reflectivity and pitch of the liquid crystal. Cholesteric liquid crystal has a responsive behavior to external stimulus, and because of this behavior, cholesteric liquid crystal is widely used in the fields of filter, information storage, display and the like.

Cholesteric liquid crystal is generally formulated from a nematic liquid crystal and a chiral additive, because chiral additive can induce the transformation of nematic liquid crystal to cholesteric liquid crystal. Therefore, chiral additive plays an important role in nematic liquid crystal. With respect to a chiral additive, helical twisting power constant (HTP) is a key parameter to evaluate its twisting capacity, and is defined as:

$$p = 1/(\text{HTP} \times Xc)$$

wherein, p is the pitch of a cholesteric liquid crystal, and Xc is the concentration by mass of a chiral additive in the host liquid crystal material. The HTP value depends on the nature of the chiral additive itself. When p is constant, the greater the HTP value of the chiral additive, the less the amount of the chiral additive in the host liquid crystal material is, which is beneficial for improving the properties of the cholesteric liquid crystal.

SUMMARY

The present disclosure provides a chiral compound, a cholesteric liquid crystal material comprising the chiral compound, preparation methods for the chiral compound and the cholesteric liquid crystal material, and a display device comprising the cholesteric liquid crystal material.

A first aspect of the present disclosure provides a chiral compound of the following formula (I):

wherein, (I)

n and n' are identical or different and are 0, 1, 2, 3, 4 or 5; and when n is greater than 1, $R^1$s each may be identical or different, and when n' is greater than 1, $R^{1'}$s each may be identical or different;

m and m' are identical or different and are 0, 1, 2, 3 or 4; and when m is greater than 1, $R^2$s each may be identical or different, and when m' is greater than 1, $R^{2'}$s each may be identical or different;

$R^1$ and $R^{1'}$ are identical or different;

$R^2$ and $R^{2'}$ are identical or different;

$R^1$, $R^{1'}$, $R^2$ and $R^{2'}$ are independently selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio, halo-$C_1$-$C_6$ alkylthio, $C_3$-$C_8$ cycloalkyl and phenyl, wherein the $C_3$-$C_8$ cycloalkyl and phenyl may further contain one or more substituents selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio and halo-$C_1$-$C_6$ alkylthio.

In one embodiment of the present disclosure, the compound of formula (I) is a compound of formula (Ia) having a trans configuration or a compound of formula (Ib) having a cis configuration:

(Ia)

(Ib)

In another embodiment of the present disclosure, $R^1$, $R^{1'}$, $R^2$ and $R^{2'}$ are independently selected from the group consisting of:

F, Cl, nitro, cyano, $C_1$-$C_4$ alkyl, halo-$C_1$-$C_4$ alkyl, $C_1$-$C_4$ alkoxy, halo-$C_1$-$C_4$ alkoxy, $C_1$-$C_4$ alkylthio, halo-$C_1$-$C_4$ alkylthio, $C_3$-$C_6$ cycloalkyl and phenyl, wherein the $C_3$-$C_6$ cycloalkyl and phenyl may further contain one or more substituents selected from the group consisting of F, Cl, nitro, cyano, $C_1$-$C_4$ alkyl, halo-$C_1$-$C_4$ alkyl, $C_1$-$C_4$ alkoxy, halo-$C_1$-$C_4$ alkoxy, $C_1$-$C_4$ alkylthio and halo-$C_1$-$C_6$ alkylthio.

In yet another embodiment of the present disclosure, n and n' are 1, and $R^1$ and $R^{1'}$ each are a substituent at para-position.

In still another embodiment of the present disclosure, n and n' are 1, m and m' are 0 or 1, and $R^1$, $R^{1'}$, $R^2$ and $R^{2'}$ are independently selected from the group consisting of —$CH_3$, —$CF_3$, —F, —$NO_2$, —$OCH_3$ and phenyl.

In still yet another embodiment of the present disclosure, $(R^1)_n$ and $(R^{1'})_n$ as well as $(R^2)_m$ and $(R^{2'})_{m'}$ are selected such that the compound of formula (I) is a symmetrical compound; for example, n=n'=1, m=m'=0, $R^1$ and $R^{1'}$ are identical and are 2-phenyl, 3-phenyl or 4-phenyl.

A second aspect of the present disclosure provides a method for preparing the compound of formula (I), comprising: subjecting a compound of formula (II) and compounds of formulae (III) and (III') to an alcohol-acid esterification reaction, or subjecting a compound of formula (II) and compounds of formulae (IV) and (IV') to an alcohol-acyl halide esterification reaction:

(II)

(III)

(III')

(IV)

(IV')

wherein $R^1$, $R^{1'}$, $R^2$, $R^{2'}$, n, n', m and m' each are as defined above, and X and X' each independently are halogen, such as chlorine or bromine.

In one embodiment of the present disclosure, the molar ratio of the compound of formula (III) to the compound of formula (III') is 1.2:1 to 1:1.2, for example 1.1:1 to 1:1.1; the molar ratio of the sum of the compound of formula (III) and the compound of formula (III') to the compound of formula (II) is 3.0:1 to 4.0:1, for example 3.1:1 to 3.5:1; the molar ratio of the compound of formula (IV) to the compound of formula (IV') is 1.2:1 to 1:1.2, for example 1.1:1 to 1:1.1; and the molar ratio of the sum of the compound of formula (IV) and the compound of formula (IV') to the compound of formula (II) is 4:1 to 4.5:1, for example 4.2:1 to 4.3:1.

In another embodiment of the present disclosure, the alcohol-acid esterification reaction is performed at a temperature of −10° C. to 55° C.; and the alcohol-acyl halide esterification reaction is performed at a temperature of 25° C. to 60° C.

In yet another embodiment of the present disclosure, the alcohol-acid esterification reaction is performed for 10-15 hours, preferably 12-13 hours; and the alcohol-acyl halide esterification reaction is performed for 10-15 hours, preferably 12-14 hours.

A third aspect of the present disclosure provides a method for preparing a cholesteric liquid crystal material, comprising mixing the compound of formula (I) according to the present disclosure with a nematic liquid crystal compound.

A fourth aspect of the present disclosure provides a cholesteric liquid crystal material comprising a nematic liquid crystal compound and the compound of formula (I) according to the present disclosure.

A fifth aspect of the present disclosure provides a display device comprising the cholesteric liquid crystal material according to the present disclosure as display material.

Further aspects and scopes of the present disclosure will become apparent from the description provided herein. It should be understood that each aspect of the present application can be implemented alone or in combination with one or more other aspects. It should be also understood that the description and particular embodiments herein are intended for illustrative purpose but not for limiting the scope of the present application.

BRIEF DESCRIPTION OF DRAWINGS

In order to more clearly illustrate the technical solutions of the embodiments of the present disclosure, brief description is made below in combination with the drawings. It should be appreciated that the drawings described below only relate to a part of embodiments of the present disclosure, but are not intended to limit the present disclosure, in which.

DETAILED DESCRIPTION

In order to make the technical solutions and advantages of the present disclosure more clear, the technical solutions of embodiments of the present disclosure will be described in detail below. Obviously, the embodiments described are only a part of, but not all of the embodiments of the present disclosure. All of other embodiments obtained by those skilled in the art based on the embodiments described, without inventive efforts, fall within the protection scope of the present disclosure.

The first aspect of the present disclosure provides a chiral compound of the following formula (I):

(I)

wherein, n and n' are identical or different and are 0, 1, 2, 3, 4 or 5; and when n is greater than 1, $R^1$'s each may be identical or different, and when n' is greater than 1, $R^{1'}$'s each may be identical or different;

m and m' are identical or different and are 0, 1, 2, 3 or 4; and when m is greater than 1, $R^2$'s each may be identical or different, and when m' is greater than 1, $R^{2'}$'s each may be identical or different;

$R^1$ and $R^{1'}$ are identical or different;

$R^2$ and $R^{2'}$ are identical or different;

$R^1$, $R^{1'}$, $R^2$ and $R^{2'}$ are selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio, halo-$C_1$-$C_6$ alkylthio, $C_3$-$C_8$ cycloalkyl and phenyl, wherein the $C_3$-$C_8$ cycloalkyl and phenyl may further contain one or more substituents selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio and halo-$C_1$-$C_6$ alkylthio. In the present disclosure, halogen includes F, Cl, Br and I. Preferably, the halogen includes F, Cl or a combination thereof. "$C_1$-$C_6$ alkyl" refers to an alkyl containing 1-6 carbon atoms in total. "Halo-$C_1$-$C_6$ alkyl" refers to a $C_1$-$C_6$ alkyl partially or fully substituted by halogen. "$C_1$-$C_6$ alkoxy" refers to an oxy group connected with a $C_1$-$C_6$ alkyl. "Halo-$C_1$-$C_6$ alkoxy" refers to an oxy group connected with a halo-$C_1$-$C_6$ alkyl. "$C_1$-$C_6$ alkylthio" refers to a thio group connected with a $C_1$-$C_6$ alkyl. "Halo-$C_1$-$C_6$ alkylthio" refers to a thio group connected with a halo-$C_1$-$C_6$ alkyl. "$C_3$-$C_8$ cycloalkyl" refers to a cyclic alkyl containing 3-8 carbon atoms.

It is found by the inventors that the compound of formula (I) is a novel photosensitive chiral agent and can be used as a chiral additive for photosensitive liquid crystal. When the compound is added to a nematic liquid crystal material, a cholesteric liquid crystal can be obtained, and moreover, the helical twisting power constant of the chiral additive can be changed by irradiating, thereby expanding the reflection band width of cholesteric liquid crystal device.

In the present disclosure, due to the presence of N=N double bond in the to compound of formula (I), this compound may have either a cis configuration or a trans configuration, that is, there are an isomer of formula (Ia) having a trans configuration and an isomer of formula (Ib) having a cis configuration:

(Ia)

(Ib)

Therefore, in one embodiment of the present disclosure, the compound of formula (I) is an isomer having a cis configuration or an isomer having a trans configuration.

In the compound of formula (I) of the present disclosure, two phenyl rings directly connected to two chiral carbon atoms respectively each can contain no substituent, or can contain 1, 2, 3, 4 or 5 identical or different substituents, preferably 0, 1 or 2 substituents. When the phenyl rings each contain more than one substituents, these substituents may be identical or different. That is, when n is greater than 1, $R^1$'s each may be identical or different; and when n' is greater than 1, $R^{1'}$'s each may be identical or different. As $R^1$ and $R^{1'}$ groups here, they may be identical or different from each other, and are selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio, halo-$C_1$-$C_6$ alkylthio, $C_3$-$C_8$ cycloalkyl and phenyl, wherein the $C_3$-$C_8$ cycloalkyl and phenyl can further contain one or more substituents selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio and halo-$C_1$-$C_6$ alkylthio. Preferably, n and n' are identical and are 1. Further preferably, $R^1$ and $R^{1'}$ each are independently selected from the group consisting of F, Cl, nitro, cyano, $C_1$-$C_4$ alkyl, halo-$C_1$-$C_4$ alkyl, $C_1$-$C_4$ alkoxy, halo-$C_1$-$C_4$ alkoxy, $C_1$-$C_4$ alkylthio, halo-$C_1$-$C_4$ alkylthio, $C_3$-$C_6$ cycloalkyl and phenyl, wherein the $C_3$-$C_6$ cycloalkyl and phenyl can further contain one or more substituents selected from the group consisting of F, Cl, nitro, cyano, $C_1$-$C_4$ alkyl, halo-$C_1$-$C_4$ alkyl, $C_1$-$C_4$ alkoxy, halo-$C_1$-$C_4$ alkoxy, $C_1$-$C_4$ alkylthio and halo-$C_1$-$C_6$ alkylthio.

In the compound of formula (I) of the present disclosure, two phenyl rings directly connected to azo nitrogen atoms respectively each can contain no substituent, or can contain 1, 2, 3 or 4 identical or different substituents, preferably 0, 1 or 2 substituents. When the phenyl rings each contain more than one substituents, these substituents may be identical or different. That is, when m is greater than 1, $R^2$s each may be identical or different; and when m' is greater than 1, $R^{2'}$'s each may be identical or different. As $R^2$ and $R^{2'}$ groups here, they may be identical or different from each other, and are selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio, halo-$C_1$-$C_6$ alkylthio, $C_3$-$C_8$ cycloalkyl and phenyl, wherein the cycloalkyl and phenyl can further contain one or more substituents selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio and halo-$C_1$-$C_6$ alkylthio. Preferably, m and m' are identical and are 1. Further preferably, $R^2$ and $R^{2'}$ each are independently selected from the group consisting of F, Cl, nitro, cyano, $C_1$-$C_4$ alkyl, halo-$C_1$-$C_4$ alkyl, $C_1$-$C_4$ alkoxy, halo-$C_1$-$C_4$ alkoxy, $C_1$-$C_4$ alkylthio, halo-$C_1$-$C_4$ alkylthio, $C_3$-$C_6$ cycloalkyl and phenyl, wherein the $C_3$-$C_6$ cycloalkyl and phenyl can further contain one or more substituents selected from the group consisting of F, Cl, nitro, cyano, $C_1$-$C_4$ alkyl, halo-$C_1$-$C_4$ alkyl, $C_1$-$C_4$ alkoxy, halo-$C_1$-$C_4$ alkoxy, $C_1$-$C_4$ alkylthio and halo-$C_1$-$C_6$ alkylthio.

In one embodiment of the present disclosure, n and n' are 1, and $R^1$ and $R^{1'}$ each are a substituent at para-position.

In one embodiment of the present disclosure, n and n' are 1, m and m' are 0 or 1, and $R^1$, $R^{1'}$, $R^2$ and $R^{2'}$ are independently selected from the group consisting of —$CH_3$, —$CF_3$, —F, —$NO_2$, —$OCH_3$ and phenyl.

In one embodiment of the compound of formula (I) of the present disclosure, the compound of formula (I) is a symmetrical compound, that is, $(R^1)_n$ and $(R^{1'})_n$ as well as $(R^2)_m$ and $(R^{2'})_m$ are selected such that the compound of formula (I) is a symmetrical compound. This means that n and n' are identical; m and m' are identical; $R^1$ and $R^{1'}$ are identical; $R^2$ and $R^{2'}$ are identical; the positions of n $R^1$ groups and n' $R^{1'}$ groups on respective phenyl rings are identical, and the positions of m $R^2$ groups and m' $R^{2'}$ groups on respective phenyl rings are identical. Likewise, when the compound of formula (I) is a symmetrical compound, if n is greater than 1, $R^1$s each may be identical or different; if n' is greater than 1, $R^{1'}$'s each may be identical or different; if m is greater than 1, $R^2$s each may be identical or different; and if m' is greater than 1, $R^{2'}$'s each may be identical or different. In one embodiment of the present disclosure, the compound of formula (I) is a symmetrical compound, wherein n and n' are 1, m and m' are 0 or 1, $R^1$ and $R^{1'}$ are identical and are selected from the group consisting of —$CH_3$, —$CF_3$, —F, —$NO_2$, —$OCH_3$ and phenyl, and $R^2$ and $R^{2'}$ are identical and are selected from the group consisting of —$CH_3$, —$CF_3$, —F, —$NO_2$, —$OCH_3$ and phenyl. In another embodiment of the present disclosure, the compound of formula (I) is a symmetrical compound, wherein n=n'=1, m=m'=0, and $R^1$ and $R^{1'}$ are identical and are 2-phenyl, 3-phenyl or 4-phenyl.

The second aspect of the present disclosure provides a method for preparing the compound of formula (I) of the present disclosure, comprising: subjecting a compound of formula (II) and compounds of formulae (III) and (III') to an alcohol-acid esterification reaction, or subjecting a compound of formula (II) and compounds of formulae (IV) and (IV') to an alcohol-acyl halide esterification reaction:

wherein $R^1$, $R^{1'}$, $R^2$, $R^{2'}$, n, n', m and m' each are as defined for the compound of formula (I), and X and X' each independently are halogen, such as chlorine or bromine.

The compound of formula (II) is a hydroxyl compound, the compounds of formulae (III) and (III') are carboxylic acid compounds, and a compound of formula (I) can be obtained through an alcohol-acid esterification reaction between them, i.e. an esterification reaction between alcohol and acid. Those skilled in the art can appreciate that when a compound of formula (I) in which $(R^1)_n$ and $(R^{1'})_{n'}$ are completely identical (including the positions of substituents) is to be prepared, the compound of formula (III) is completely identical to the compound of formula (III'), and the compound of formula (I) in this case can be obtained by subjecting the compound of formula (II) and the compound of formula (III) or (III') to an alcohol-acid esterification reaction; when a compound of formula (I) in which $(R^1)_n$ and $(R^{1'})_{n'}$ are not completely identical (including the positions of substituents) is to be prepared, the compound of formula (III) is not identical to the compound of formula (III'), and in this case it is required to subject the compound of formula (II) and a mixture of the compound of formula (III) and the compound of formula (III') to an alcohol-acid esterification reaction.

The compounds of formulae (IV) and (IV') are acyl halide compounds, and a compound of formula (I) can be obtained through an alcohol-acyl halide esterification reaction between the compound of formula (II) and the compounds of formulae (IV) and (IV'), i.e. an esterification reaction between alcohol and acyl halide. Those skilled in the art can appreciate that when a compound of formula (I) in which $(R^1)_n$ and $(R^{1'})_{n'}$ are completely identical (including the positions of substituents) is to be prepared, the compound of formula (IV) is completely identical to the compound of formula (IV'), and the compound of formula (I) in this case can be obtained by subjecting the compound of formula (II) and the compound of formula (IV) or (IV') to an alcohol-acyl halide esterification reaction; when a compound of formula (I) in which $(R^1)_n$ and $(R^{1'})_{n'}$ are not completely identical (including the positions of substituents) is to be prepared, the compound of formula (IV) is not identical to the compound of formula (IV'), and in this case it is required to subject the compound of formula (II) and a mixture of the compound of formula (IV) and the compound of formula (IV') to an alcohol-acyl halide esterification reaction.

The reaction between the compound of formula (II) and the compounds of formulae (III) and (III') is a conventional alcohol-acid esterification reaction, and the reaction conditions are not particularly limited, as long as the compound of formula (I) can be obtained after the reaction. Generally, this reaction is performed in an organic solvent in the presence of an alcohol-acid esterification catalyst. The organic solvent is not particularly limited, as long as the desired alcohol-acid esterification reaction can occur. As an example, the solvent may be tetrahydrofuran and/or chloroform or the like. The alcohol-acid esterification catalyst is not particularly limited, as long as the desired alcohol-acid esterification reaction can occur. As an example, the alcohol-acid esterification catalyst may be concentrated sulfuric acid. The alcohol-acid esterification reaction can be advantageously performed under an inert atmosphere. The inert atmosphere is not particularly limited, as long as the gas does not involve in the alcohol-acid esterification reaction. As an example, the inert atmosphere may be nitrogen, argon, helium, neon or the like. It is advantageous in the alcohol-acid esterification reaction that the sum of the compounds of formulae (III) and (III') is generally excessive with respect to the compound of formula (II). Generally, the molar ratio of the sum of the compounds of formulae (III) and (III') to the compound of formula (II) may be 3.0:1 to 4.0:1, preferably 3.1:1 to 3.5:1, for example 3.2:1. The compound of formula (III) and the compound of formula (III') are generally used in substantially equal molar ratio, preferably in a molar ratio of 1.2:1 to 1:1.2, particularly preferably in a molar ratio of 1.1:1 to 1:1.1. The temperature for the alcohol-acid esterification reaction is not particularly limited, as long as the alcohol-acid esterification reaction can occur to obtain the compound of formula (I). It is preferable that the alcohol-acid esterification reaction is performed at a temperature of −10° C. to 55° C., for example under conditions of reflux by heating. The pressure for the alcohol-acid esterification reaction is not particularly limited, and the reaction is generally performed under a normal pressure. The duration of the alcohol-acid esterification reaction is generally 10-15 hours, preferably 12-13 hours. It is advantageous that the alcohol-acid esterification reaction is performed with stirring. After the alcohol-acid esterification reaction is completed, the resulting reaction product mixture is subjected to a post-treatment to isolate the compound of formula (I). Generally, the reaction product mixture is required to be purified, for example by extracting, then it is washed and subsequently dried, to obtain the compound of formula (I).

The reaction between the compound of formula (II) and the compounds of formulae (IV) and (IV') is a conventional alcohol-acyl halide esterification reaction, and the reaction conditions are not particularly limited, as long as the compound of formula (I) can be obtained after the reaction. Generally, this reaction is performed in an organic solvent under an inert atmosphere. The organic solvent is not particularly limited, as long as the desired alcohol-acyl halide esterification reaction can occur. As an example of the solvent, tetrahydrofuran and/or chloroform may be mentioned. The inert atmosphere is not particularly limited, as long as the gas does not involve in the alcohol-acyl halide esterification reaction. As an example of the inert atmosphere, nitrogen, argon, helium, neon or the like may be mentioned. It is advantageous in the alcohol-acyl halide esterification reaction that the sum of the compounds of formulae (IV) and (IV') is generally excessive with respect to the compound of formula (II). Generally, the molar ratio of the sum of the compounds of formulae (IV) and (IV') to the compound of formula (II) may be 4:1 to 4.5:1, preferably 4.2:1 to 4.3:1, for example 4.2:1. The compound of formula (IV) and the compound of formula (IV') are generally used in substantially equal molar ratio, preferably in a molar ratio of 1.2:1 to 1:1.2, particularly preferably in a molar ratio of 1.1:1 to 1:1.1. The temperature for the alcohol-acyl halide esterification reaction is not particularly limited, as long as the alcohol-acyl halide esterification reaction can occur to obtain the compound of formula (I). It is preferable that the alcohol-acyl halide esterification reaction is performed at a temperature of 25-60° C., for example under conditions of reflux by heating. The pressure for the alcohol-acyl halide esterification reaction is not particularly limited, and the reaction is generally performed under a normal pressure. The duration of the alcohol-acyl halide esterification reaction is generally 10-15 hours, preferably 12-14 hours. It is advantageous that the alcohol-acyl halide esterification reaction is performed with stirring. After the alcohol-acyl halide esterification reaction is completed, the resulting reaction product mixture is subjected to a post-treatment to isolate the compound of formula (I). Generally, the reaction product mixture is required to be purified, for example washed, distilled and subsequently dried, to obtain the compound of formula (I).

In one embodiment of the present disclosure, the acyl halide compounds of formulae (IV) and (IV') are prepared by subjecting the carboxylic acid compounds of formulae (III) and (III') to a halogenation reaction with a halogenating agent respectively.

As the halogenating agent used for this halogenation reaction, conventional halogenating agents, for example dihalosulfoxide such as dichlorosulfoxide, t-butyl hypochlorite, and halogen, which can convert a carboxylic acid to an acyl halide, may be used. A chlorinating agent or brominating agent is preferably used. The halogenation reaction is generally performed in an organic solvent under an inert atmosphere. The organic solvent is not particularly limited, as long as the desired halogenation reaction can occur. As an example of the solvent, tetrahydrofuran, chloroform or the like may be mentioned. The inert atmosphere is not particularly limited, as long as the gas does not involve in the halogenation reaction. As an example of the inert atmosphere, nitrogen, argon, helium, neon or the like may be mentioned. The halogenating agent used for halogenating the compound of formula (III) or (III') is generally excessive with respect to the compound of formula (III) or (III'), and the molar ratio of the former to the latter may generally be 3:1 to 3.8:1, preferably 3.2:1 to 3.5:1. The temperature for the halogenation reaction is not particularly limited, as long as the halogenation reaction can occur to obtain the compound of formula (IV) or (IV'). It is preferable that the halogenation reaction is performed at a temperature of −10° C. to 55° C., for example in ice bath. The duration of the halogenation reaction is generally 8-12 hours, preferably 9-11 hours.

After the halogenation reaction is completed, it is advantageous that the resulting reaction product mixture is subjected to a post-treatment to isolate the compound of formula (IV) or (IV'). Generally, the reaction product mixture is required to be purified, for example distilled, extracted, then distilled again, and subsequently dried, to obtain the compound of formula (IV) or (IV').

The presence of azo double bond in the compound of formula (I) of the present disclosure results that this compound has a cis configuration and a trans configuration. The molecular configuration of the compound of formula (I) can be adjusted with the wavelength and intensity of the irradiated light, and the cis and trans configurations can be converted reversibly, that is, the cis configuration can be converted to the trans configuration, or the trans configuration can be converted to the cis configuration, wherein the configuration conversion is controlled by the wavelength, and the conversion rate is controlled by the intensity of the irradiated light. The inventors of the present disclosure firstly discover that the polarities and chiralities of these two configurational isomers are different, which can be used to reversibly adjust the pitch of the cholesteric liquid crystal such that the cholesteric liquid crystal obtained by adding the compound of formula (I) to a nematic liquid crystal will produce different reflected lights under the same visible light irradiation, allowing the cholesteric liquid crystal device to achieve a light-induced color change (photochromism).

The trans configuration of formula (Ia) can be converted to the cis configuration of formula (Ib) under ultraviolet (UV) light irradiation, while the cis configuration of formula (Ib) can be converted to the trans configuration of formula (Ia) under visible (Vis) light irradiation. The conversion between these two configurations is reversible, and can be represented by the following equation (1):

(1)

Therefore, the third aspect of the present disclosure provides a method for preparing a cholesteric liquid crystal material, comprising mixing the compound of formula (I) of the present disclosure with a nematic liquid crystal compound.

The fourth aspect of the present disclosure provides a cholesteric liquid crystal material comprising a nematic liquid crystal compound and the compound of formula (I) of the present disclosure. This cholesteric liquid crystal material can expand the reflection band width due to containing the compound of formula (I) of the present disclosure.

The fifth aspect of the present disclosure provides a display device comprising the cholesteric liquid crystal material of the present disclosure as display material. This display device can expand the reflection band width due to containing the cholesteric liquid crystal material prepared with the compound of formula (I) of the present disclosure.

The above display device may be any product or component having a displaying function such as liquid crystal panel, mobile phone, tablet computer, television, display, notebook, digital photo frame, navigator and the like.

In the present disclosure, the nematic liquid crystal compound or material, which is mixed with the compound of formula (I) to obtain the cholesteric liquid crystal material, is not particularly limited. As an example, E7 (a nematic biphenyl mixed liquid crystal, produced by Jiangsu Hecheng New Material Co, Ltd., Product No. E7) may be mentioned. Generally, the compound of formula (I) of the present disclosure is contained in the nematic liquid crystal compound in an amount of 0.01% to 10% by weight, based on the total weight of the nematic liquid crystal compound.

The reversible conversion of the molecular structure of the compound of the present disclosure under ultraviolet and visible light irradiation can be verified as follows:

The compound of formula (I) is formulated into a solution in tetrahydrofuran at a concentration of $2 \times 10^{-5}$ mol/L, heated for 8 h, and then irradiated with an ultraviolet light of 365 nm; ultraviolet and visible absorption spectra of the solution at different exposure times are measured until the spectra will not change. At this time the molecule is in the cis state, i.e. becomes the compound of formula (Ib). Then, the solution is irradiated with a visible light of 440 nm; ultraviolet and visible absorption spectra of the solution at different exposure times are measured until the spectra will not change; and at this time the molecule is in the trans state, i.e. becomes the compound of formula (Ia). The change in the molecular structure results in the change in ultraviolet light absorption capacity of the molecule.

The photosensitive chiral macrocyclic molecule of the present disclosure has cis-trans isomerism, and due to the difference in polarities and configurations of the two isomers, it can be used to adjust the pitch of the cholesteric liquid crystal, which can be verified as follows:

0.001 g of the compound of formula (I) is added to 0.100 g of a nematic liquid crystal, the mixture is heated to clarity, and then incubated in a darkroom for 1 hour. After that, it is injected into a wedge liquid crystal cell wherein α=0.01° (here, angle α refers to an angle included between the top and bottom glass plates of the wedge cell); the pitch after irradiating with a light of 365 nm wavelength for 100 s is measured with a polarization microscope, and then the pitch after irradiating with a visible light of 440 nm wavelength for 300 s is measured. This process has a rapid response and is reversible.

It is found that when the chiral molecule of the present disclosure and a nematic liquid crystal are mixed and injected into an antiparallel liquid crystal cell (i.e., a liquid crystal cell in which the rubbing directions on polyimide (PI) are parallel with each other), the orientation of the nematic liquid crystal molecule is induced by the photosensitive chiral molecule with trans configuration to form a cholesteric phase; after treating sufficiently in darkness, the reflection band width of the liquid crystal device is adjusted to red light region, resulting in a reflection wavelength within 640-780 nm; when a white light is incident on the liquid crystal device, the device reflects red light. Then, if a ultraviolet light of 365 nm is used to irradiate the cholesteric liquid crystal device, the content of the photosensitive chiral molecule with cis configuration (converted from the photosensitive chiral molecule with trans configuration) will increase over time. At this time, the pitch p of the cholesteric liquid crystal increases, and the reflection band width is blue shifted, resulting in a reflection wavelength within 450-500 nm, so that the device shows a blue light reflection. Subsequently, the device is irradiated again with a visible light of 440 nm. This process is reversible and rapid. Therefore, the chiral molecule of formula (I) of the present disclosure can be used for light-driven liquid crystal pitch change, and thus be used to adjust the reflection band width of a cholesteric liquid crystal device.

Figure 1:
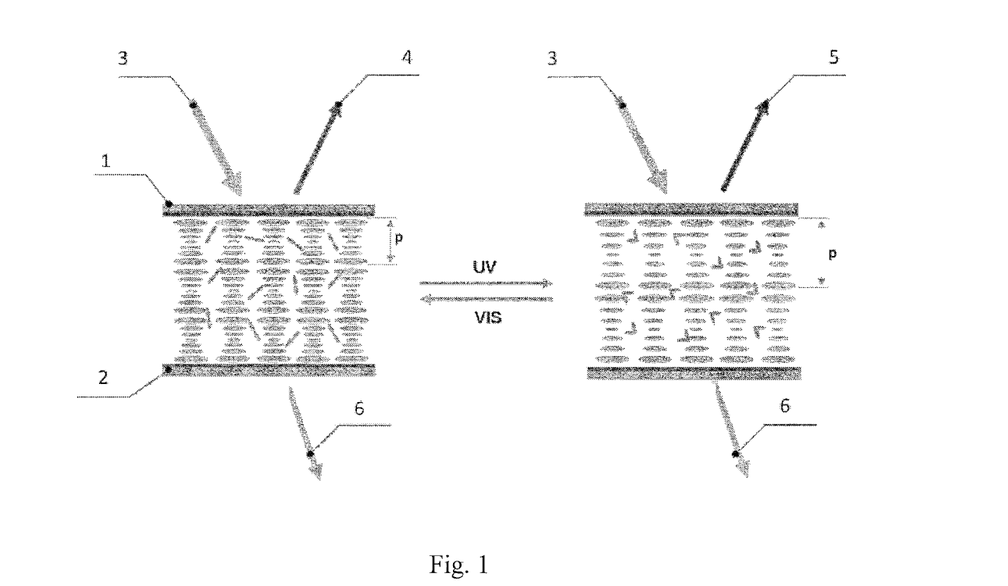
FIG. 1 is a schematic diagram showing how a chiral molecule of formula (I) adjusts the reflection band width of a liquid crystal device.

The schematic diagram showing that the chiral molecule having two isomeric states of the present disclosure can be used to adjust the photo-response of a liquid crystal device is shown in FIG. 1. The reference numbers and symbols in FIG. 1 represent the following meanings:
1: top substrate
2: bottom substrate
3: white incident light
4: red reflected light
5: blue reflected light
6: white transmitted light
∽∽: liquid crystal molecule
⌿: molecule with trans configuration
⌡: molecule with cis configuration The advantageous effects of the present disclosure include the following:
1) the preparation of the new material is simple;
2) the material has a good compatibility with liquid crystal molecule;
3) the photo-response is rapid;
4) the helical twisting power constant to liquid crystal is large;
5) it can achieve the reversible adjustment of the pitch of cholesteric liquid crystal by irradiating the new photosensitive molecule with lights of different wavelengths, enabling the cholesteric liquid crystal device to achieve light-induced color change; and
6) the thermal stability is good.

EXAMPLES

Experiment of Change in Cis-Trans Configurations

The compound of formula (I) was formulated into a solution in tetrahydrofuran at a concentration of $2\times10^{-5}$ mol/L, heated for 8 h, and then irradiated with an ultraviolet light of 365 nm; ultraviolet and visible absorption spectra of the solution at different exposure times were measured until the spectra would not change. The azo compound was generally converted into a cis configuration under irradiation with ultraviolet light, that is, became the compound of formula (Ib). Then, the solution was irradiated with a visible light of 440 nm; ultraviolet and visible absorption spectra of the solution at different exposure times were measured until the spectra would not change; and at this time the molecule was in the trans configuration, i.e. became the compound of formula (Ia).

Experiment of Reversible Change in Cis-Trans Configurations

2 mg of the compound of formula (I) were weighed and formulated into a solution in tetrahydrofuran at a concentration of $2\times10^{-5}$ mol/L. This solution was irradiated with an ultraviolet light of 365 nm until the spectrum of the solution would not change, and then was irradiated with a visible light of 440 nm until the spectrum of the solution would not change; then again this solution was irradiated with an ultraviolet light of 365 nm until the spectrum of the solution would not change, and was irradiated with a visible light of 440 nm until the spectrum of the solution would not change. Such process was repeated, and the spectral absorption values at 336 nm and 440 nm were recorded.

Experiment of Adjusting Pitch of Cholesteric Liquid Crystal

0.001 g of the compound of formula (I) was added to 0.100 g of a nematic liquid crystal (a nematic biphenyl mixed liquid crystal, produced by Jiangsu Hecheng, Product No. E7), and the mixture was heated to clarity, incubated in a darkroom for 1 hour, and then injected into a wedge liquid crystal cell wherein α=0.01°. The pitch after irradiating with a light of 365 nm for 100 s was measured with a polarization microscope, and then the pitch after irradiating with a visible light of 440 nm instead for 300 s was measured; and such process was repeated.

Example 1: compound of formula (I) wherein n and n' are 1, m and m' are 0, both $R^1$ and $R^{1'}$ are 4-phenyl 1 g of (S)-3-methyl-3-(4-phenyl)phenylpropionic acid of the following formula and dichlorosulfoxide in a molar ratio or 1:3:8 were mixed in 60 ml tetrahydrofuran and stirred for 10 h in ice bath under nitrogen protection. Then, the solvent was distilled off at normal temperature and reduced pressure, and the residue was dissolved in dichloromethane, extracted with 10% by weight of aqueous hydrochloric acid solution (3×30 ml), then extracted with 10% by weight of aqueous sodium hydroxide solution (3×30 ml), and dried by adding 5 g of magnesium sulfate. The magnesium sulfate was then filtered out, and the dichloromethane was distilled off at normal temperature and reduced pressure, to obtain an intermediate, 1.3 g in total. This intermediate was 3-methyl-3-(4-phenyl)phenylpropionyl chloride of the following formula, having a specific optical rotation of −21.5° measured with an optical rotation tester at 25° C.

The resulting intermediate compound and 2,2'-dihydroxyazobenzene in a molar ratio of 4.2:1 were dissolved in 60 ml tetrahydrofuran, and the solution was heated to 55° C. and refluxed at this temperature for 13 h. Then, the resulting reaction product mixture was washed with a mixture of petroleum ether:ethyl acetate in a weight ratio of 4:1 as eluent, then distilled at normal temperature and reduced pressure to distill off the solvent, and the residue was dried, to obtain the product, 1.7 g in total. This product had a specific optical rotation of −10.8° measured with an optical rotation tester at 25° C., and was identified as the title compound via infrared spectrum. The structural formula of the product was as follow (referred as compound A hereinafter):

A

IR (KBr, cm$^{-1}$): 3057, 1480, 1275, 1244, 1051, 750.

Figure 2:
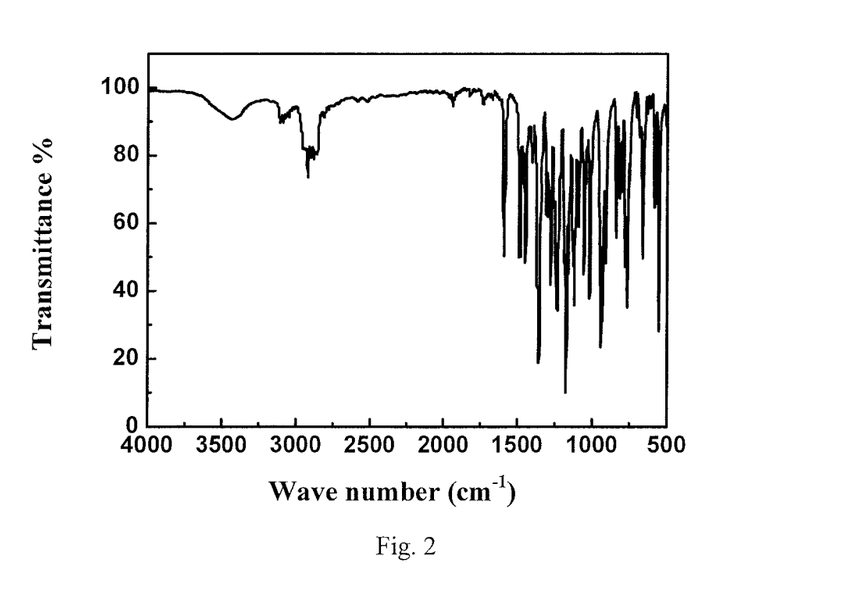
FIG. 2 is an infrared spectrum of the compound of formula (I) prepared in Example 1.

The infrared spectrum of compound A is shown in FIG. 2.

Figure 3:
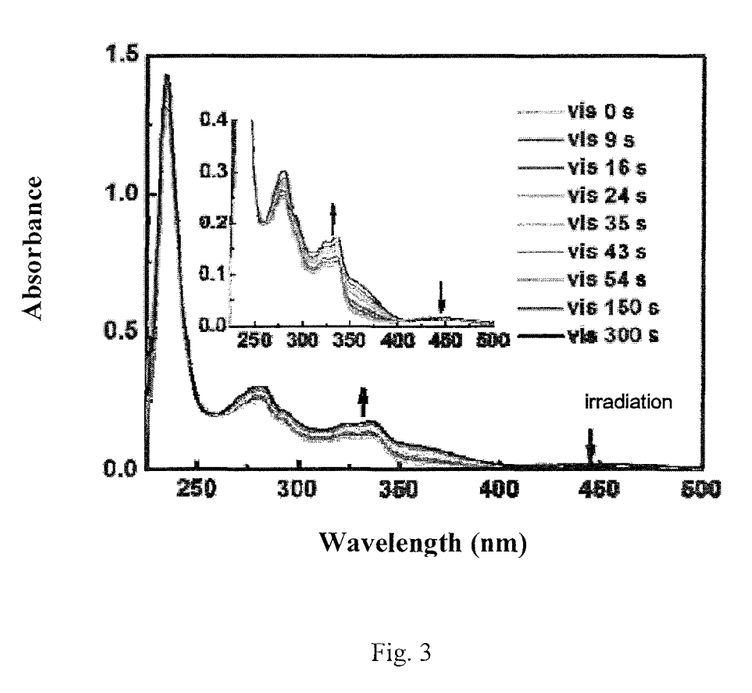
FIG. 3 is an ultraviolet-visible absorption spectrum of the compound of formula (I) prepared in Example 1 at different exposure times.

Compound A was subjected to the "experiment of change in cis-trans configurations" described above, and the spectrum obtained was shown in FIG. 3. As seen from FIG. 3, as the time for irradiation with the visible light of 440 nm increased, the absorption value around 336 nm increased gradually, and the curve around there raised gradually, while the absorption value around 440 nm decreased gradually, and the curve around there declined gradually. As such, under irradiation with the visible light of 440 nm, the absorption value at 336 nm of the solution of compound A increased gradually, while the absorption value at 440 nm decreased gradually as time went on, proving that the configuration of the molecule of compound A had been changed under visible light irradiation.

Figure 4:
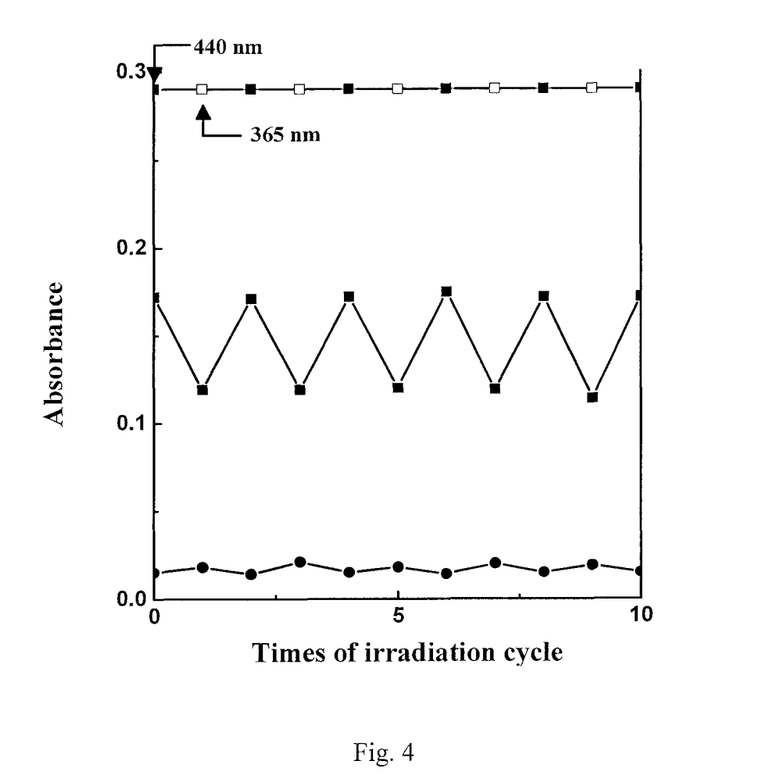
FIG. 4 shows spectral absorption curves of a solution of the compound of formula (I) prepared in Example 1 in tetrahydrofuran at 336 nm and 440 nm under irradiation with lights of different wavelengths.

Compound A was subjected to the "experiment of reversible change in cis-trans configurations" described above, and the result obtained was shown in FIG. 4. There were three curves in FIG. 4, wherein the upmost one was a curve with alternative solid squares and hollow squares indicating that the solution was irradiated with the visible light of 440 nm and the ultraviolet light of 365 nm respectively to reach absorption saturation, that is, until the spectral absorption value would not change; the middle curve with solid squares recorded the spectral absorption values of the solution at 336 nm; and the bottom curve with solid circles recorded the spectral absorption values of the solution at 440 nm. As can be seen from FIG. 4, the absorption values of the ultraviolet-visible absorption spectrum of the solution of compound A fluctuated regularly along with the switch between irradiated light of different wavelengths.

Figure 5:
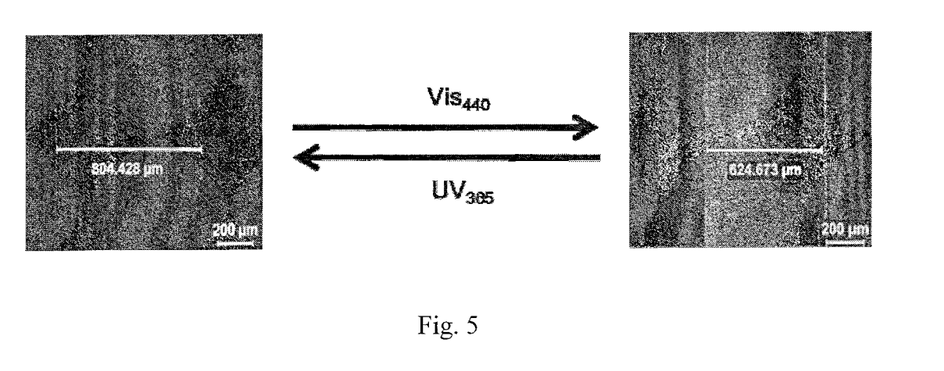
FIG. 5 shows the change in the pitch of a nematic liquid crystal mixture containing 1% by mass of the compound of formula (I) prepared in Example 1 in a wedge cell under irradiation with lights of different wavelengths.

Compound A was subjected to the "experiment of adjusting the pitch of a cholesteric liquid crystal" described above, and the result obtained was shown in FIG. 5. As can be seen from FIG. 5, the interference fringe, i.e. the pitch of the cholesteric liquid crystal, in the wedge cell changed along with irradiated lights of different wavelengths, indicating that the twisting power constant of the molecule changed, wherein the pitch after irradiating with the light of 365 nm for 100 seconds was 804.428 μm, and the pitch after irradiating with the visible light of 440 nm for 300 seconds was 624.673 μm, and such pitch changes were regularly reversed.

It can be understood that the above embodiments are only exemplary embodiments for illustrating the principle of the present disclosure, but the present disclosure is not limited thereto. For those skilled in the art, various variations and modifications can be made without departing from the spirit and essence of the present disclosure, and these variations and modifications also fall within the protection scope of the present disclosure.

What is claimed is:

1. A chiral compound having a structure represented by the following formula (I):

(I)

wherein, n and n' are identical or different and are 0, 1, 2, 3, 4 or 5; and when n is greater than 1, R$^1$s each may be identical or different, and when n' is greater than 1, $R^{1'}$'s each may be identical or different;

m and m' are identical or different and are 0, 1, 2, 3 or 4; when m is greater than 1, $R^2$s each may be identical or different, and when m' is greater than 1, $R^{2'}$'s each may be identical or different;

$R^1$ and $R^{1'}$ are identical or different;

$R^2$ and $R^{2'}$ are identical or different;

$R^1$, $R^{1'}$, $R^2$ and $R^{2'}$ are independently selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio, halo-$C_1$-$C_6$ alkylthio, $C_3$-$C_8$ cycloalkyl and phenyl, wherein the $C_3$-$C_8$ cycloalkyl and phenyl may further contain one or more substituents selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio and halo-$C_1$-$C_6$ alkylthio.

2. The compound according to claim 1, wherein the compound is a compound of formula (Ia) having a trans configuration or a compound of formula (Ib) having a cis configuration:

(Ia)

(Ib)

3. The compound according to claim 1, wherein $R^1$, $R^{1'}$, $R^2$ and $R^{2'}$ are independently selected from the group consisting of:

F, Cl, nitro, cyano, $C_1$-$C_4$ alkyl, halo-$C_1$-$C_4$ alkyl, $C_1$-$C_4$ alkoxy, halo-$C_1$-$C_4$ alkoxy, $C_1$-$C_4$ alkylthio, halo-$C_1$-$C_4$ alkylthio, $C_3$-$C_6$ cycloalkyl and phenyl, wherein the $C_3$-$C_6$ cycloalkyl and phenyl may further contain one or more substituents selected from the group consisting of F, Cl, nitro, cyano, $C_1$-$C_4$ alkyl, halo-$C_1$-$C_4$ alkyl, $C_1$-$C_4$ alkoxy, halo-$C_1$-$C_4$ alkoxy, $C_1$-$C_4$ alkylthio and halo-$C_1$-$C_6$ alkylthio.

4. The compound according to claim 1, wherein n and n' are 1, and $R^1$ and $R^{1'}$ each are a substituent at para-position.

5. The compound according to claim 1, wherein n and n' are 1, m and m' are 0 or 1, and $R^1$, $R^{1'}$, $R^2$ and $R^{2'}$ are independently selected from the group consisting of —$CH_3$, —$CF_3$, —F, —$NO_2$, —$OCH_3$ and phenyl.

6. The compound according to claim 1, wherein $(R^1)_n$ and $(R^{1'})_n$ as well as $(R^2)_m$ and $(R^{2'})_m$ are selected such that the compound of formula (I) is a symmetrical compound.

7. A method for preparing a compound of formula (I):

(I)

wherein the method comprises subjecting a compound of formula (II) and compounds of formulae (III) and (III') to an alcohol-acid esterification reaction, or subjecting a compound of formula (II) and compounds of formulae (IV) and (IV') to an alcohol-acyl halide esterification reaction:

(II)

(III)

(III')

(IV)

(IV')

wherein, n and n' each are as defined in claim 1, n and n' are identical or different and are 0, 1, 2, 3, 4 or 5; and when n is greater than 1 $R^1$s each may be identical or different, and when n' is greater than 1, each may be identical or different;

m and m' are identical or different and are 0, 1, 2, 3 or 4; when m is greater than 1, $R^2$s each may be identical or different, and when m' is greater than 1, $R^2$s each may be identical or different;

$R^1$ and $R^{1'}$ are identical or different:

$R^2$ and $R^{2'}$ are identical or different;

$R^1$, $R^{1'}$, $R^2$ and $R^{2'}$ are independently selected from the group consisting of halogen nitro, cyano, $C_1$-$C_6$ alkyl, halo-$C_1$-$C_6$ alkoxy, halo-$C_1$-$C_6$ alkoxy, $C_1$-$C_6$ halo-$C_1$-$C_6$ alkylthio, $C_3$-$C_8$ cycloalkyl and phenyl, wherein the $C_3$-$C_8$ cycloalkyl and phenyl may further contain one or more substituents selected from the group consisting of halogen, nitro, cyano, $C_1$-$C_6$ alkyl, halo-$C_1$-$C_6$ alkyl, $C_1$-$C_6$ alkoxy, halo-$C_1$-$C_6$ alkoxy, $C_1$-$C_6$ alkylthio and halo-$C_1$-$C_6$ alkylthio, and X and X' each independently are halogen.

8. The method according to claim 7, wherein the molar ratio of the compound of formula (III) to the compound of formula (III') is 1.2:1 to 1:1.2; the molar ratio of the sum of the compound of formula (III) and the compound of formula (III') to the compound of formula (II) is 3.0:1 to 4.0:1; the molar ratio of the compound of formula (IV) to the compound of formula (IV') is 1.2:1 to 1:1.2; and the molar ratio of the sum of the compound of formula (IV) and the compound of formula (IV') to the compound of formula (II) is 4:1 to 4.5:1.

9. The method according to claim 7, wherein the alcohol-acid esterification reaction is performed at a temperature of −10° C. to 55° C.; and the alcohol-acyl halide esterification reaction is performed at a temperature of 25° C. to 60° C.

10. The method according to claim 7, wherein the alcohol-acid esterification reaction is performed for 10-15 hours; and the alcohol-acyl halide esterification reaction is performed for 10-15 hours.

11. A method for preparing a cholesteric liquid crystal material, comprising mixing the compound of formula (I) of claim 1 with a nematic liquid crystal compound.

12. A cholesteric liquid crystal material comprising a nematic liquid crystal compound and the compound of formula (I) of claim 1.

13. A display device comprising the cholesteric liquid crystal material of claim 12 as display material.

14. The compound according to claim 6, wherein n=n'=1, m=m'=0, $R^1$ and $R^{1'}$ are identical and are 2-phenyl, 3-phenyl or 4-phenyl.

15. A cholesteric liquid crystal material comprising a nematic liquid crystal compound and the compound of formula (I) of claim 4.

16. A cholesteric liquid crystal material comprising a nematic liquid crystal compound and the compound of formula (I) of claim 5.

17. A cholesteric liquid crystal material comprising a nematic liquid crystal compound and the compound of formula (I) of claim 6.

18. A cholesteric liquid crystal material comprising a nematic liquid crystal compound and the compound of formula (I) of claim 14.

19. The cholesteric liquid crystal material according to claim 12, wherein a pitch of the cholesteric liquid crystal in the cholesteric liquid crystal material is reversibly adjustable by irradiating.

20. The cholesteric liquid crystal material according to claim 19, wherein the irradiating includes irradiating the cholesteric liquid crystal material with an ultraviolet light and a visible light respectively.

\* \* \* \* \*